United States Patent
Thomas et al.

(10) Patent No.: US 11,779,527 B2
(45) Date of Patent: Oct. 10, 2023

(54) USEFUL COMPOSITIONS FOR THE COSMETIC TREATMENT OF OILY SKIN

(71) Applicant: TOMCAT INTERNATIONAL LIMITED, London (GB)

(72) Inventors: Mathilde Thomas, Paris (FR); Bertrand Thomas, Paris (FR)

(73) Assignee: TOMCAT INTERNATIONAL LIMITED, London (GB)

( * ) Notice: Subject to any disclaimer, the term of this patent is extended or adjusted under 35 U.S.C. 154(b) by 213 days.

(21) Appl. No.: 16/960,753

(22) PCT Filed: Jan. 9, 2018

(86) PCT No.: PCT/EP2018/050482
§ 371 (c)(1),
(2) Date: Jul. 8, 2020

(87) PCT Pub. No.: WO2019/137603
PCT Pub. Date: Jul. 18, 2019

(65) Prior Publication Data
US 2020/0337967 A1  Oct. 29, 2020

(51) Int. Cl.
```
A61K 8/34       (2006.01)
A61K 8/9789     (2017.01)
A61K 8/92       (2006.01)
A61Q 19/00      (2006.01)
```

(52) U.S. Cl.
CPC .............. *A61K 8/347* (2013.01); *A61K 8/922* (2013.01); *A61K 8/9789* (2017.08); *A61Q 19/008* (2013.01)

(58) Field of Classification Search
CPC .................................................. A61Q 19/08
See application file for complete search history.

(56) References Cited

U.S. PATENT DOCUMENTS

| | | | |
|---|---|---|---|
| 10,231,921 | B2 | 3/2019 | Lerebour et al. |
| 2004/0234480 | A1 | 11/2004 | Pauly et al. |
| 2005/0261367 | A1* | 11/2005 | Murad ............ A61Q 19/00 514/561 |
| 2016/0095812 | A1 | 4/2016 | Lerebour et al. |
| 2019/0151232 | A1* | 5/2019 | Scharp ............ A61K 31/245 |

FOREIGN PATENT DOCUMENTS

| | | |
|---|---|---|
| FR | 2715848 A1 | 8/1995 |
| FR | 2770228 A1 | 4/1999 |
| FR | 2836377 A1 | 8/2003 |
| FR | 3004937 A1 | 10/2014 |
| FR | 3004939 A1 | 10/2014 |
| FR | 3006890 A1 | 12/2014 |
| GB | 2469289 A | 10/2010 |
| KR | 1020170058546 A * | 5/2017 |
| KR | 101787406 B1 * | 10/2017 |
| WO | WO 2011/128714 A1 | 10/2011 |

OTHER PUBLICATIONS

International Search Report dated Sep. 25, 2018 issued in PCT/EP2018/050482.
Thomson Scientific, London, GB; AN 2015-05076R, XP002784662, Nov. 19, 2014.
"Step 03 Medicated Acne care Essence", Oct. 1, 2013, XP002784663.

* cited by examiner

*Primary Examiner* — Gina C Justice
(74) *Attorney, Agent, or Firm* — Scully, Scott, Murphy & Presser, P.C.

(57) ABSTRACT

The invention relates to the cosmetic use of an association of (i) at least one polyphenol selected from the monomers and oligomers of flavonoids extracted from vines, the derivatives thereof and the mixtures thereof, and (ii) at least two essential oils selected from peppermint, geranium, lemon balm, lemongrass, rosemary and lavender, for treating and/or preventing oily skin or skin with oily tendencies and/or aesthetic skin problems associated therewith. The invention also relates to a cosmetic method for treating oily skin, and to compositions containing the association. It also relates to the association of polyphenols and the mixture of essential oils for treating acne or skin with oily tendencies.

6 Claims, 1 Drawing Sheet

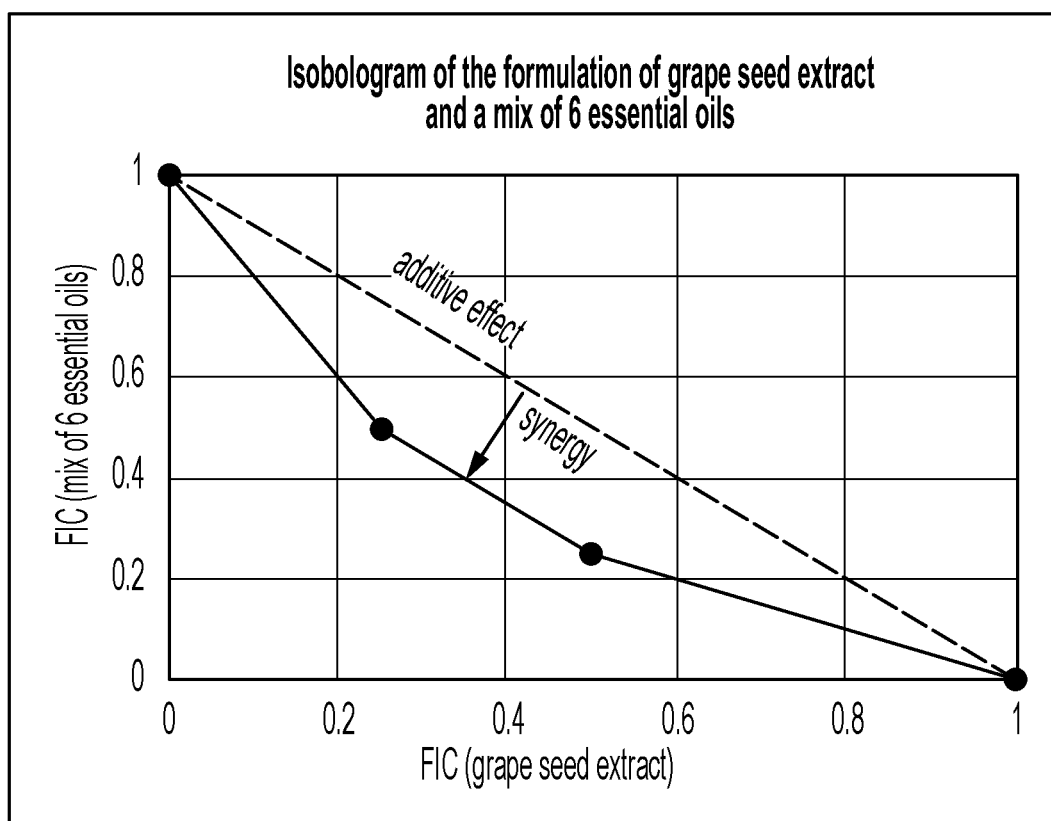

USEFUL COMPOSITIONS FOR THE COSMETIC TREATMENT OF OILY SKIN

The present invention relates to improving the appearance of oily skin or skin with oily tendencies and of signs of skin problems associated therewith. It thus relates to new active associations that can be used for this purpose and have synergistic activity, and to compositions containing said associations. The invention also relates to the cosmetic use of such associations and compositions for treating oily skin and skin with oily tendencies, and to methods for the cosmetic treatment of skin of this kind.

According to another aspect, the invention relates to the treatment and/or prevention of acne and acne-prone skin problems.

The skin naturally secretes an oily substance, called sebum, which normally constitutes a hydrating agent for the epidermis and may be involved in the homeostasis of the epidermis. It contributes to the protection thereof against environmental damage, by means of antioxidant or antimicrobial activity in particular.

Sebum is the natural product of the sebaceous gland, which forms an annex of the pilosebaceous unit. It is essentially a more or less complex mixture of lipids. Oily or hyperseborrheic skin is characterized in particular by the excessive secretion and excretion of sebum. Conventionally, a sebum rate of greater than 220 µg/cm$^2$ measured in the region of the forehead is considered characteristic of this oily skin.

Oily skin is a common cosmetic problem which occurs when the sebaceous glands produce excess sebum (seborrheic skin), giving the skin an oily, shiny appearance. This phenomenon is also associated with an increase in the size of the pores, a rough and uneven skin texture, and blackheads, which are considered to be skin imperfections and cosmetic defects.

The sebaceous glands which produce sebum are found in the reticular dermis, where they are associated with hairs, and together form the pilosebaceous units. The density of the pilosebaceous glands varies significantly according to their position on the body. They are abundant in the region of the face, in particular in the region of the forehead, nose and chin (T zone), as well as in the region of the scalp. These zones are therefore also the zones most often associated with oily skin problems.

There are many factors that may contribute to the increase in seborrhea, including hormonal factors, genetics, age, gender, ethnicity, climatic variations, pollution, stress, tiredness, and the microbiome, for example.

Oily skin is generally healthy skin which effectively resists the signs of aging, for example; it does not develop into other conditions. However, its appearance, which is deemed unsightly, and the skin imperfections that may be present result in a need to seek solutions for treating them and combating the signs and disorders associated therewith.

Oily skin or skin with oily tendencies and the cosmetic defects or skin imperfections thereof may be associated with the growth of *Propionibacterium acnes* germs, besides excess sebum. The *Propionibacterium acnes* (*P. acnes*) germ is part of the Gram-positive anaerobic bacteria that prefer to grow in oxygen-deficient environments, such as at the bottom of a hair follicle or blocked sebaceous duct.

*Propionibacterium acnes* contributes to the problem of non-acne-prone oily skin with imperfections. Indeed, in subjects who were in good health and did not have a history of skin disorders, an increase in the quantity of sebum correlated with an increase in the prevalence of *Propionibacterium* and a decrease in microbial diversity. Likewise, a correlation was demonstrated between the prevalence of *Propionibacterium acnes* and the quantity of skin lipids produced in subjects who were in good health and did not have a history of skin disorders. Lastly, it was demonstrated that *Propionibacterium acnes* may contribute directly to an increase in lipogenesis and therefore to an increase in sebum production.

Moreover, acne is a common inflammatory condition that affects the pilosebaceous follicle, in which *Propionibacterium acnes* is involved. It is characterized by the presence of retentional lesions (micro-cysts) and/or inflammatory lesions (papules, pustules, nodules). The etiopathology of acne has multiple factors, and remains partly unknown. However, the quantity and quality of the sebum plays a key role in the proliferation of the *Propionibacterium acnes* bacteria which contributes to the inflammatory skin condition.

FR 3 006890 proposes the cosmetic use of dermicidin for the prevention or treatment of oily skin.

The use of essential oils has also been proposed to combat the signs of skin problems associated with oily skin. For example, FR 3 004937 relates to the cosmetic use of an *Origanum majorana* essential oil; FR 3 004939 describes the use of *Satureja montana* essential oil for the cosmetic treatment of oily skin.

CN104146915 describes a cosmetic article for hydrating the skin which has anti-acne activity, containing a mixture of essential oils.

However, there is still a need to provide new active substances that have improved cosmetic efficacy for sebum production and the signs associated with increased sebum production.

Unexpectedly, it has now been found that a association of polyphenols and a mixture of essential oils has a synergistic action for inhibiting the growth of *P. acnes* and thus makes it possible to effectively combat the cosmetic defects associated with oily skin or skin with oily tendencies.

For this reason, the present invention relates to the cosmetic use of an association of (i) at least one polyphenol selected from monomeric and oligomeric flavonoids extracted from vines, the derivatives and mixtures thereof, and (ii) at least two essential oils, and preferably at least three essential oils, selected from peppermint, geranium, lemon balm, lemongrass, rosemary and lavender essential oils, for treating and/or preventing oily skin or skin with oily tendencies and/or aesthetic skin problems associated therewith.

The invention also relates to a method for the cosmetic treatment of oily skin or skin with oily tendencies and/or aesthetic skin problems associated with oily skin or skin with oily tendencies, which includes the topical application to the skin of an association of (i) at least one polyphenol and (ii) a mixture of at least two essential oils selected from peppermint, geranium, lemon balm, lemongrass, rosemary and lavender essential oils, or of a cosmetic composition containing said association.

The invention also relates to a composition, in particular a cosmetic composition, containing an association of this kind in a physiologically acceptable medium; the composition is preferably suitable for topical application to the skin. In particular, the cosmetic composition may contain an association of (i) at least one polyphenol selected from monomeric and oligomeric flavonoids extracted from vines, the derivatives and mixtures thereof, and
(ii) at least two essential oils, and preferably at least three essential oils, selected from peppermint, geranium, lemon balm, lemongrass, rosemary and lavender essential oils, in a physiologically acceptable medium.

The invention is also directed to an association (i) of at least one polyphenol extracted from vines (*Vitis vinifera*) and (ii) a mixture of at least two essential oils, in particular at least three essential oils, selected from peppermint (*Mentha piperita*), geranium (*Pelargonium graveolens*), lemon balm (*Melissa officinalis*), lemongrass (*Cymbopogon flexuosus*), rosemary (*Rosmarinus officinalis*) and lavender (*Lavandula hybrida*) essential oils, for use in the treatment of hyperseborrheic skin and/or acne-prone skin, or acne, and/or of signs of skin problems linked thereto.

The polyphenols suitable for use in the invention are selected from monomeric and oligomeric flavonoids extracted from vines.

They may be obtained from different parts of the *Vitis vinifera* plant, for example the whole grape, or parts of the fruit such as the skin, the grape seeds, the pulp or the grape juice, but also other parts of the plant (vine shoots, leaves, flowers, etc.).

Advantageously, polyphenols extracted from grape seeds or grape juice, or derivatives thereof, are used.

These polyphenols may be in the native or stabilized form.

The polyphenols suitable for the invention are flavonoids, such as monomeric and oligomeric flavan-3-ols, in particular catechin, epicatechin, gallocatechins, epigallocatechins (for example epigallocatechin gallate) and oligomeric proanthocyanidin or OPC, anthocyanins or flavanones; flavonols, dihydroflavonols, flavones and isoflavones can also be added.

Advantageously, the polyphenols or polyphenol derivatives contain catechins and/or oligomeric catechins, or derivatives of these compounds.

Oligomeric catechins preferably contain 2 to 6 catechin units (catechin or epicatechin) and are also called OPCs.

The monomeric units of the flavonoids have the following structure (I)

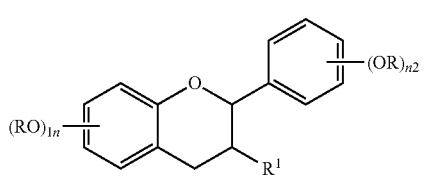

(I)

in which
R1 represents an —OR2 group, a hydrogen atom, or an R3 substitute; R2 and R3 are identical or different, and are as defined below for R4
at least the majority of R substitutes represent a —COR4 group, R4 being an alkyl radical of at least two linear or branched, saturated or unsaturated carbon atoms, an aryl, arylalkyl or arylalkylene radical,
the R substitute(s) which does/do not represent a —COR4 group is/are a hydrogen atom or an alkyl group, and n1 and n2, which are identical to or different from one another, are numbers from 1 to 3, corresponding to the number of substitutions on one cycle,
the monomer units being connected in the oligomers and polymers by carbon-carbon bonds and/or an ether bridge between the units.

In the oligomers and polymers of the invention, the bonds between the carbon atoms of successive units are situated between the C-4 of one unit and the C-6 or C-8 of another unit.

In other oligomers and polymers, at least 2 units are also connected by an oxygen bridge.

In a preferred composition, the polyphenols are flavonoid extracts from the vine and, more specifically, from grape seeds (OPC), containing monomers, oligomers and/or polymers of units having formula (I).

"Polyphenol derivatives" means, more particularly, stabilized molecules in which all or some of the hydroxyl groups are etherified or esterified. According to a preferred embodiment, the esterification is formed with a saturated or unsaturated fatty acid. The fatty acid may in particular be selected from butyric acid, valeric acid, hexanic acid, sorbic acid, lauric acid, palmitic acid, stearic acid, oleic acid, linoleic acid, linolenic acid, alpha-linolenic acid, arachidonic acid, eicosapentaenoic acid and docosahexaenoic acid.

According to a particular embodiment, all the hydroxyl groups of the polyphenol are esterified or etherified, and therefore the polyphenol derivative no longer has a free OH function. Such ethers or esters may in particular be prepared using the method described in the application WO 2011/128714.

The association according to the invention contains in particular at least one polyphenol selected from monomeric and oligomeric flavan-3-ols, such as monomeric and oligomeric proanthocyanidins (OPC), the derivatives and mixtures thereof in all proportions. Advantageously, in a composition according to the invention, the polyphenols mentioned in (i) contain OPCs extracted from grape seeds. In particular, the association or composition contains polyphenol derivatives, which are polyphenol esters.

According to a particular embodiment, the polyphenols are present in the association or composition in the form of grape seed extracts, potentially stabilized in order to obtain polyphenol derivatives in said extracts.

Such polyphenols generally comprise at least 20% (by weight, relative to the total weight of polyphenols) of monomeric and/or dimeric catechins; for example, the content of proanthocyanidin dimers is greater than or equal to 20% (by weight, relative to the total weight of polyphenols), and/or the content of [catechin and epicatechin] is greater than or equal to 20% (by weight, relative to the total weight of polyphenols).

According to another embodiment, the polyphenols are extracted from grape pulp or grape juice.

According to an advantageous embodiment, at least one polyphenol is selected from monomeric and oligomeric proanthocyanidins extracted from grapes, in native form or esterified form, and mixtures thereof.

Such polyphenols extracted from vines have an inhibitor effect on the growth of *P. acnes*.

The other constituent of the association according to the invention is a mixture of essential oils selected from the group comprising peppermint (*Mentha piperita*), geranium (*Pelargonium graveolens*), lemon balm (*Melissa officinalis*), lemongrass (*Cymbopogon flexuosus*), rosemary (*Rosmarinus officinalis*) and lavender (*Lavandula hybrida*) essential oils.

Indeed, a combination of these essential oils is particularly effective for limiting or inhibiting the growth of *P. acnes*, the presence of this microorganism being correlated with signs of oily skin or skin with oily tendencies.

Furthermore, it has been found within the context of the invention that the inhibiting activity on the growth of *P. acnes* is enhanced in a synergistic manner by an association of this mixture of essential oils with polyphenols extracted from vines, as specified above.

The essential oils are products obtained from raw materials of plant origin (leaves, stalks, flowers or the whole plant, for example).

These essential oils can be obtained in accordance with different methods, such as steam distillation, and volatile-solvent distillation or extraction in particular. According to the definition given in the international ISO 9235 standard and adopted by the European Pharmacopoeia Commission, an essential oil is an odorant product that generally has a complex composition, and is obtained from a botanically defined raw plant material, either by steam distillation, by dry distillation, or using an appropriate mechanical method without heating (cold expression). The essential oil is usually separated from the aqueous phase by a physical process that does not result in a significant change in the composition.

Of the methods for obtaining an essential oil, steam distillation can be mentioned, which may for example be carried out by dry distillation or hydrodistillation.

Hydrodistillation can be carried out on a glass apparatus, such as that defined in the European Pharmacopoeia, for determining the essential oil of a plant material. Steam distillation corresponds to the vaporization, in the presence of steam, of a substance which is not very miscible with water. The raw material is brought together with boiling water (hydrodistillation) or steam in a still (dry distillation). The steam carries along the essential oil vapor, which is condensed in the refrigerant in order to be collected in liquid phase in a Florentine vase (or an essencier), where the essential oil is separated from the water by decanting. The aqueous distillate which remains upon steam distillation once the essential oil has been separated is called "aromatic water" or "hydrolate" or "distilled floral water." The essential oils are generally volatile and liquid at room temperature (25° C.), which differentiates them from oils known as "fixed oils." They differ in color intensity and their density is generally less than that of water. They are liposoluble and soluble in the usual organic solvents, can be steam-distilled and are very poorly soluble in water.

Geranium essential oil is extracted from plants of the genus *Pelargonium*, from the Geraniaceae family. An essential oil extracted from the flowers of *Pelargonium graveolens* is used in particular.

Mint (of the genus *Mentha*) is a plant from the Lamiaceae family. Peppermint essential oil extracted from the species *Mentha piperita* is used in particular. The essential oil preferably comes from the tops of the plant.

Lemongrass is a plant from the Poaceae (grasses) family. Lemongrass essential oil is extracted from the species *Cymbopogon flexuosus*. It comes from the herbaceous parts of the plant, in particular the leaves.

Lemon balm is a plant from the genus *Melissa* from the Lamiaceae family. The essential oil extracted from the *Melissa officinalis* plant, preferably from the aerial parts and the leaves of the plant, is used in particular.

Rosemary, or *Rosmarinus officinalis*, is a shrub from the Lamiaceae family. The essential oil extracted from the aerial parts, in particular the flowering tops of the plant, is used in particular.

Lavender (*Lavandula hybrida*) comes from a lavender hybrid. The essential oil extracted from the aerial parts, in particular the flowering tops of the plant, is used in particular.

Preferably, for carrying out the invention, a mixture of at least two, in particular at least three or at least four essential oils selected from the group of mint, in particular peppermint, geranium, lemon balm, lemongrass, rosemary and lavender essential oils is used. The association may in particular contain at least 5 essential oils, and according to a particular embodiment, a mixture of the 6 essential oils from the above-mentioned plants.

It is understood that the invention comprises mixtures of different essential oils in all proportions.

The proportions of each of the essential oils in the mixture of essential oils would be adjusted by a person skilled in the art.

Geranium essential oil (*Pelargonium graveolens*) can constitute from 0 to 50% of the mixture of essential oils; when it is present in the mixture, it can, for example, constitute from 1 to 50 vol. % of the mixture of essential oil present in the association according to the invention, in particular from 5 to 45%, in particular from 30 to 45%.

Peppermint essential oil (*Mentha piperita*) can constitute from 0 to 50% of the mixture of essential oils; when it is present in the mixture, it can, for example, constitute from 1 to 50 vol. % of the mixture of essential oils present in the association according to the invention, in particular from 5 to 40%, in particular from 20 to 35%.

Lemongrass essential oil (*Cymbopogon flexuosus*) can constitute from 0 to 50% of the mixture of essential oils; when it is present in the mixture, it can, for example, constitute from 1 to 50 vol. % of the mixture of essential oils present in the association according to the invention, in particular from 5 to 30%, in particular from 15 to 22%.

Lemon balm essential oil (*Melissa officinalis*) can constitute from 0 to 50% of the mixture of essential oils; when it is present in the mixture, it can, for example, constitute from 1 to 40 vol. % of the mixture of essential oils present in the association according to the invention, in particular from 1 to 30%, in particular from 2 to 15%.

Rosemary essential oil (*Rosmarinus officinalis*) can constitute from 0 to 50% of the mixture of essential oils; when it is present in the mixture, it can, for example, constitute from 1 to 40 vol. % of the mixture of essential oils present in the association according to the invention, in particular from 5 to 20%, in particular from 10 to 17%.

Lavender essential oil (*Lavandula hybrida*) can constitute from 0 to 50% of the mixture of essential oils; when it is present in the mixture, it can, for example, constitute from 1 to 40 vol. % of the mixture of essential oils present in the association according to the invention, in particular from 2 to 20%, in particular from 4 to 10%.

A mixture of essential oils suitable for carrying out the invention contains, for example, from 20 to 35% peppermint essential oil, from 30 to 45% geranium essential oil, from 2 to 15% lemon balm essential oil, from 15 to 22% lemongrass essential oil, from 10 to 17% rosemary essential oil, and from 4 to 10% lavender essential oil.

Throughout the description, the expressions "between . . . and . . . " and "from . . . to . . . " should be understood to be inclusive, unless specified otherwise.

Unless specified otherwise, the uses and methods according to the invention are of a cosmetic, non-therapeutic nature; they essentially have an aesthetic purpose.

"Prevent" or "prevention" means reducing the probability of occurrence or reducing the signs of the problem in question.

"Treat" means eliminating, limiting or slowing the signs of the problem in question.

The association defined above, or the cosmetic composition containing said association, is particularly useful in treating or preventing aesthetic skin problems which are skin imperfections selected from shiny skin, oily skin, skin having dilated follicular openings or pores, skin having blackheads and/or pimples, a thick skin texture, rough skin or skin having an uneven surface.

The invention makes it possible in particular to treat or prevent aesthetic skin problems which are imperfections associated with the growth of *Propionibacterium acnes.*

A composition that is particularly suitable for the invention contains, in a physiologically, and in particular cosmetically, acceptable medium, a synergistic association for inhibiting the growth of *P. acnes* of (i) polyphenols extracted from vines and/or any of its derivatives and (ii) a mixture of essential oils, as specified above.

In a composition of this kind, the polyphenol(s) or polyphenol derivatives extracted from vines may be present in a concentration of from 0.01 to 10%, in particular of from 0.02 to 10%; according to certain embodiments, the concentration of polyphenols and in particular OPCs extracted from grapes is less than 1%, and in particular from 0.01 to 0.5% by weight relative to the total weight of the composition.

The mixture of essential oils selected from the group specified above may be present in the compositions according to the invention at a concentration that for example varies from 0.02 to 5%, in particular from 0.02 to 1% by weight, but this concentration may be greater than or equal to 0.04% by weight; in particular, the concentration of the mixture of essential oils may vary from 0.04 to 0.5%, in particular from 0.04 to 0.4% by weight.

The percentages are expressed by weight relative to the total weight of the composition.

The invention thus relates to a composition which contains at least:
  (i) one polyphenol selected from monomeric and oligomeric proanthocyanidins extracted from grapes, in native form or esterified form, and mixtures thereof, and
  (ii) a mixture of peppermint, geranium, lemon balm, lemongrass, rosemary and lavender essential oils, the mixture of essential oils.

A composition according to the invention in particular contains at least:
  (i) one grape pip extract containing polyphenols, stabilized by esterification, the extract being present in a concentration of from 0.01 to 10% by weight relative to the total weight of the composition, and
  (ii) a mixture of peppermint, geranium, lemon balm, lemongrass, rosemary and lavender essential oils, said mixture of essential oils being present in a concentration of from 0.01 to 10% by weight relative to the total weight of the composition.

In associations that are particularly suitable for carrying out the invention, the mass ratio of grape polyphenols to essential oils is between 1:100 and 100:1. Advantageously, the mass ratio of grape polyphenols to essential oils is between 1:50 and 50:1, in particular between 1:25 and 25:1. It may in particular vary from 4:1 to 1:4, and in particular may be 1:1.

The compositions according to the invention are preferably cosmetic compositions or dermatological compositions suitable for application to the skin or skin appendages. The composition according to the invention contains the association of polyphenols or polyphenol derivatives extracted from vines and essential oils as specified above, and a physiologically acceptable medium.

"Physiologically acceptable medium" means a medium that is compatible with the skin or skin appendages and does not cause an undesirable effect when it comes into contact with the different parts of the body.

It is in particular a cosmetically acceptable medium. This therefore means a medium or excipients that are well tolerated by the skin and have a pleasant odor and appearance.

"Cosmetic product" or "cosmetic composition" means a substance or mixture intended to come into contact with the surface parts of the human body or with the teeth or buccal mucosae, with a view to, exclusively or primarily, cleaning them, perfuming them, modifying the appearance thereof, protecting them, keeping them in good condition or rectifying body odors. A cosmetic treatment method within the meaning of the invention has the same aims.

The composition may be more or less fluid and may have the appearance of a white or colored cream, an ointment, a milk, a lotion, a serum, a paste, or a mousse. It may also be in solid form, in particular in the form of a stick. It may be used as a care product and/or as a make-up product and/or as a hygiene product for the skin or skin appendages.

The composition according to the invention may be in any of the galenic forms that are normally used in the cosmetic field, and it may in particular be in the form of a potentially gelled aqueous or oily solution, a potentially two-phase lotion-type dispersion, an emulsion obtained by dispersing a fatty phase in an aqueous phase (O/W) or vice versa (W/O), or a triple emulsion (W/O/W or O/W/O), or an ionic and/or non-ionic vesicular dispersion. These compositions are prepared in accordance with the standard methods.

If the composition used according to the invention is an emulsion, the proportion of the fatty phase may be from 0.5 to 80% by weight, and preferably from 5 to 50% by weight relative to the total weight of the composition. The oils, emulsifiers and co-emulsifiers used in the composition in the form of an emulsion are selected from those conventionally used in the field in question. The emulsifier and the co-emulsifier are present in the composition in a proportion of from 0.1 to 30% by weight, and preferably from 0.5 to 20% by weight relative to the total weight of the composition.

Oils that can be used in the invention may be hydrocarbons of mineral origin (mineral oil) or synthetic origin (vaseline oil, isohexadecane), oils of plant origin (apricot seed oil, grape seed oil, liquid fraction of shea butter, avocado oil, soybean oil), oils of animal origin (lanolin), synthetic oils (perhydrosqualene, pentaerythrityl tetraoctanoate), silicone derivatives (cyclopentasiloxane, cyclohexasiloxane, dimethicone and silicone polymers), and fluorinated oils (perfluoropolyethers). Fatty alcohols (cetyl alcohol or stearyl alcohol), fatty acids (stearic acid), waxes (carnauba wax, ozokerite, beeswax), butters, and hydrogenated oils can also be used as fats.

Fatty acid polyethylene glycol esters such as PEG-100 stearate and PEG-20 stearate and glycerin fatty acid esters such as glyceryl stearate, sucrose esters and phospholipids can for example be mentioned as emulsifiers and co-emulsifiers that can be used in the invention.

In a known manner, the composition used according to the invention may also contain conventional adjuvants in the cosmetic field, such as hydrophilic or lipophilic gellants, hydrophilic or lipophilic active substances, preservatives, antioxidants, solvents, fragrances, fillers, filters, screens, pigments, odor absorbers, chelating agents, alcohols, and colorants. The quantities of these different adjuvants are those conventionally used in the field in question, and for example from 0.01 to 20% of the total weight of the composition. Depending on their nature, these adjuvants may be added to the fatty phase, the aqueous phase or the lipid vesicles. In any case, these adjuvants and the proportions thereof would be selected so as not to affect the sought properties of the association.

Hydrophilic gellants may in particular be carboxyvinyl polymers (carbomers), acrylic copolymers such as acrylate/alkylacrylate copolymers, polyacrylamides, polysaccharides, natural rubbers and clays, and lipophilic gellants may be modified clays such as bentones, metal salts of fatty acids, hydrophobic silica, and polyethylenes.

Fillers may be, for example, polyamide particles (nylon) in spherical form or in microfiber form; polymethyl methacrylate microspheres; powders of ethylene acrylate copolymer; expanded powders such as hollow microspheres and, in particular, microspheres made of a vinylidene chloride terpolymer, acrylonitrile and methacrylate and marketed under the name EXPANCEL by Kemanord Plast; powders of natural organic materials such as starch powders, in particular maize starch, wheat starch or rice starch, which are cross-linked or non-cross-linked, such as starch powders cross-linked by octenyl succinic anhydride; silicone-resin microbeads such as those marketed under the name TOSPEARL by Toshiba Silicone; silica; metal oxides such as titanium dioxide or zinc oxide; mica; and mixtures thereof.

The composition used according to the invention may also contain at least one additional active substance. This additional active substance may in particular be an additional active substance for the treatment of oily skin. The additional active substance may in particular be a compound selected from exfoliation agents, antimicrobial agents, soothing agents, anti-inflammatory agents, antioxidant agents, healing agents, astringent agents, hydrating agents, agents promoting skin microcirculation; depigmentation agents; anti-pollution and/or anti-free-radical agents, sun filters, agents modifying sebum production, refreshing agents, and mixtures thereof.

The exfoliation agent may in particular be selected from beta hydroxy acids such as salicylic acid or an acyl derivative of salicylic acid, in particular a 5-acyl-salicylic acid such as n-octanoyl-5-salicylic acid, n-dodecanoyl-5-salicylic acid and n-decanoyl-5-salicylic acid, in free or salified form, in particular in the form of salts obtained by salification with a mineral or organic base. Other exfoliating agents that can be used are alpha hydroxy acids (AHA), such as glycolic acid, citric acid, lactic acid, tartaric acid, malic acid or mandelic acid, gentisic acid and the esters thereof, in particular tocopherol gentisate, oligofucoses, cinnamic acid, certain derivatives of jasmonic acid, and/or the derivatives and/or mixtures thereof, sugar derivatives such as O-octanoyl-6-D-maltose and N-acetyl glucosamine.

In particular, salicylic acid can be used.

Antioxidant agents may in particular be tocopherol and the esters thereof, in particular tocopherol acetate; ascorbic acid and the derivatives thereof, in particular magnesium ascorbyl phosphate, ascorbyl glucoside and ascorbyl tetraisopalmitate; ferulic acid; serine; ellagic acid, phloretin, chelating agents, such as BHT, BHA, N,N'-bis-(3,4,5-trimethoxybenzyl) ethylenediamine and the salts thereof, hydroxymatairesinol and mixtures thereof.

Advantageously, the composition according to the invention contains at least one active substance selected from exfoliation agents, antioxidant agents and soothing agents.

In particular, the cosmetic composition according to the invention further contains at least one active substance selected from vitamin C and the derivatives thereof and vitamin E or the derivatives thereof, such as tocopherol acetate.

Other additional active substances advantageously contained in the compositions according to the invention are selected from salicylic acid, vitamin B3 and/or rose hydrolate, and mixtures thereof.

The additional active substances may be present in the composition according to the invention in a content of from 0.001 to 20% by weight relative to the total weight of the composition, preferably from 0.01% to 10%, more preferably from 0.5% to 5% and yet more preferably from 0.1 to 1% by weight relative to the total weight of the composition.

The invention also relates to a method for cosmetic treatment, comprising a step of applying the association or compositions according to the invention to the skin or skin appendages.

The method according to the invention may prove to be particularly useful for preventing and/or treating cosmetic defects of oily skin or skin with oily tendencies, in particular for treating skin having dilated follicular openings or pores or for preventing this problem, in particular for reducing the appearance and/or visibility of the pores, for tightening the pores and/or reducing the size of the pores, and/or reducing the number of visible pores, for preventing and/or treating skin having follicular openings or pores filled with blackheads, or skin having blackheads and/or pimples. The method according to the invention may also prove to be useful for treating and/or preventing skin defects or imperfections associated with the growth of *Propionibacterium acnes* germs.

The invention also relates to the association of (i) at least one polyphenol selected from monomeric and oligomeric flavonoids extracted from vines, the derivatives and mixtures thereof, and (ii) at least two essential oils, and preferably at least three essential oils, selected from peppermint, geranium, lemon balm, lemongrass, rosemary and lavender essential oils, as specified above, for use in the treatment of hyperseborrheic skin and/or acne-prone skin or acne.

In this context, the association may be present in compositions containing a physiologically acceptable medium as specified above.

The compositions and associations according to the invention may be applied directly to the skin or skin appendages or, alternatively, to occlusive or non-occlusive cosmetic or dermatological carriers, intended to be applied to the skin in a localized manner, such as hydrogel masks, wipes, tissues, or biocellulose.

It may be applied daily, multiple times a day, or weekly, for example. This may carry on for several days and/or several weeks, or even longer; it may be continued or, for example, carried on for 1 to 2 months, and then restarted after pausing.

The cosmetic composition may be rinsed off or not rinsed off after being applied to the skin. Moreover, after application of the cosmetic composition according to the invention, a composition containing one or more active substances selected from antibacterial agents, antifungal agents and/or powders may be applied to the surface of the skin.

The invention also relates to the use of an association of (i) polyphenol selected from monomeric and oligomeric flavonoids extracted from vines, the derivatives and mixtures thereof, and (ii) at least two essential oils, and preferably at least three essential oils, selected from peppermint, geranium, lemon balm, lemongrass, rosemary and lavender essential oils as specified in the present text, for the preparation of a composition, in particular a cosmetic composition. The composition is suitable for application to the skin or skin appendages. The composition advantageously makes it possible to combat the signs linked to the proliferation of P. acnes on the skin.

The invention also relates to a method for preparing a cosmetic composition comprising a step of mixing together an effective quantity of (i) polyphenol selected from monomeric and oligomeric flavonoids extracted from vines, the derivatives and mixtures thereof, and (ii) at least two essential oils, and preferably at least three essential oils, selected from peppermint, geranium, lemon balm, lemongrass, rosemary and lavender essential oils as specified in the present text, and optionally a physiologically acceptable excipient.

Other features and advantages of the invention are illustrated in the following examples.

In these examples, reference is made to a single accompanying FIGURE. This FIGURE is an isobologram showing the synergistic effect of a grape seed extract in combination with a mix of 6 essential oils.

EXAMPLE 1

Activity on P. acnes

The antimicrobial activity of two active substances is evaluated:
- a grape seed extract
- a mixture of peppermint, geranium, lemon balm, lemongrass, rosemary and lavender essential oils The grape seed extract is metered to 97% oligomeric proanthocyanidins (OPCs).

The antimicrobial activity was tested on the bacteria Propionibacterium acnes ATCC6919, a reference strain that is sensitive to antibiotics.

The bacteria were cultivated in a brain heart infusion (BHI) liquid nutrient medium; the cultures were incubated anaerobically at 36° C. for 3 to 5 days.

In order to evaluate the antimicrobial activity of the ingredients individually, a minimum inhibitory concentration (MIC) test was carried out. The MIC measurement is an international reference method for quantifying antimicrobial activity in a liquid medium. The test was carried out on 96-well microplates. 100 µl of product to be tested (double the concentration of the concentration to be tested) was brought into contact with 100 µl of nutrient broth (at double concentration) containing the bacteria at a density of $2\text{-}6.10^5$ ufc/ml.

After incubating the microplate for 3-5 days, the bacterial growth was evaluated by measuring the optical density at 620 nm. The results are expressed in a growth percentage calculated relative to a growth control, according to the following equation:

$$\text{Growth percentage} = \frac{\text{Measured OD of product tested} - \text{OD of absorption control}}{\text{OD of growth control}}$$

where: absorption control=100 µl nutrient medium without bacteria+100 µl product to be tested
growth control=100 µl nutrient medium with bacteria+diluting solvent of the products to be tested The first concentration in the tested product that allows a growth percentage of less than or equal to 20% is considered to be inhibitory.

Antimicrobial activity on the growth of P. acnes was observed with the 2 compounds tested. The MICs measured are:
MIC (grape seed extract)=0.05% (m/v)
MIC (mix of 6 essential oils)=0.1% (m/v)

The activity of the association was evaluated in accordance with the same experiment protocol and by using the chessboard method for selecting the concentrations to be tested (MIC/4-MIC/2-MIC-2MIC-4 MIC for each of the two compounds).

In order to evaluate potential synergy between the two compounds, the fractional inhibitory concentration (FIC) was calculated:

$$\text{FIC index}=\text{FIC}_A+\text{FIC}_B$$

Where:

$$\text{FIC}_A=\text{MIC}_{A\ with\ B}/\text{MIC}_A$$

$$\text{FIC}_B=\text{MIC}_{B\ with\ A}/\text{MIC}_B$$

$\text{MIC}_{A\ with\ B}$: Concentration of product A in the association making it possible to obtain the inhibitory effect
$\text{MIC}_{B\ with\ A}$: Concentration of product B in the association making it possible to obtain the inhibitory effect
$\text{MIC}_A$: MIC of product A only
$\text{MIC}_B$: MIC of product B only According to this method, if:
FIC index≤0.75 a synergistic effect of the 2 compounds is concluded
FIC index=1 an additive effect of the 2 compounds is concluded
1≤FIC index<2 an indifference in the association of the 2 compounds is concluded
FIC index≥2 antagonism between the 2 compounds is concluded At the ratio of grape seed extract to mix of essential oils of 1:1, the following is demonstrated:
$\text{FIC}_A=0.5$ and $\text{FIC}_B=0.25$ FIC index (grape seed extract+mix of 6 essential oils)=0.75

At the ratio of grape seed extract to mix of essential oils of 1:4, the following is demonstrated:
$\text{FIC}_A=0.25$ and $\text{FIC}_B=0.5$ FIC index (grape seed extract+mix of 6 essential oils)=0.75

This result therefore proves a synergistic interaction.

A representative isobologram is shown in the accompanying FIGURE. The profile of the isobologram is different depending on the type of interaction between the ingredients. The dashed line indicates the FIC values equal to 1 which indicate a purely indifferent interaction. A concave isobologram highlights that the response of the association of the two ingredients is greater than the sum of their individual responses, which corresponds to a synergistic interaction. A convex isobologram highlights that the response of the association of the two ingredients is less than the sum of their individual responses, which corresponds to an antagonistic interaction.

The FIGURE demonstrates synergistic antimicrobial activity of the combination of the grape seed extract and the mix of essential oils against *P. acnes*.

EXAMPLE 2

Compositions

| Lotion | |
|---|---|
| Common name | % |
| Water | QSF 100 |
| Glycerin | 5.00 |
| Polyphenol vine extracts | 0.01-1% |
| Mixture of essential oils | 0.02-1% |
| Alcohol | 10.00 |

The different constituents of the composition are mixed to obtain a lotion. This is to be applied in the morning and/or evening to the whole face and the neck, avoiding the contours of the eyes.

| Cream gel | |
|---|---|
| Common name | % |
| Water | QSF 100 |
| Butylene glycol | 2.00 |
| C10/30 alkyl acrylates crosspolymer | 0.25 |
| Xanthan gum | 0.15 |
| Hexyldecanol | 3.00 |
| Salicylic acid | 0.1 |
| Sodium hyaluronate | 0.2 |
| Polyphenol vine extracts | 0.01-1% |
| Mixture of essential oils | 0.02-1% |
| Alcohol | 5.00 |

The cream gel is to be applied in the morning and/or evening to the whole face and the neck, avoiding the contours of the eyes.

| Emulsion | |
|---|---|
| Common name | % |
| Water | QSF 100 |
| Xanthan gum | 0.30 |
| Phytic acid | 0.05 |
| Salicylic acid | 0.1 |
| Coco-caprylate/caprate | 3.00 |
| Caprylic/capric triglyceride | 5.0 |
| Mixture of C14-22 alcohol and C12-20 alkyl glucoside | 3.00 |
| Polyphenol vine extract | 0.01-1% |
| Mixture of essential oils | 0.02-1% |
| Mattifying powder | 2.0 |
| Alcohol | 5 |

The emulsion is to be applied in the morning and/or evening to the whole face and the neck, avoiding the contours of the eyes.

The invention claimed is:

1. A cosmetic anti-acne composition containing an association of
   (i) at least one polyphenol selected from monomeric and oligomeric flavonoids extracted from grape seed extract, the derivatives and mixtures thereof, and
   (ii) a mixture of peppermint, geranium, lemon balm, lemongrass, rosemary and lavender essential oils,
in a physiologically acceptable medium, wherein the weight ratio of (i) to (ii) is 1:1 to 1:4.

2. The composition of claim 1, characterized in that it further contains at least one active substance selected from exfoliation agents and antioxidant agents and soothing agents.

3. The cosmetic composition of claim 1, characterized in that it contains at least
   (iii) one polyphenol selected from monomeric and oligomeric proanthocyanidins extracted from grape seed, in native form or esterified form, and mixtures thereof, and
   (iv) the mixture of peppermint, geranium, lemon balm, lemongrass, rosemary and lavender essential oils.

4. The cosmetic composition of claim 1, characterized in that it contains at least
   (iii) one grape seed extract containing polyphenols, stabilized by esterification, the extract being present in a concentration of from 0.01 to 10% by weight relative to the total weight of the composition, and
   (iv) the mixture of peppermint, geranium, lemon balm, lemongrass, rosemary and lavender essential oils, said mixture of essential oils being present in a concentration of from 0.02 to 10% by weight relative to the total weight of the composition.

5. The cosmetic composition of claim 1, wherein the at least one polyphenol is stabilized by etherification or esterification.

6. The cosmetic composition of claim 1 having an antimicrobial activity to *Propionibacterium acnes*.

* * * * *